United States Patent
Kim et al.

(10) Patent No.: US 12,142,350 B2
(45) Date of Patent: Nov. 12, 2024

(54) METHOD FOR PREDICT AFFINITY BETWEEN DRUG AND TARGET SUBSTANCE

(71) Applicant: DEARGEN INC., Daejeon (KR)

(72) Inventors: Yeachan Kim, Gyeonggi-do (KR); Bonggun Shin, Gyeongsangbuk-do (KR)

(73) Assignee: DEARGEN INC., Daejeon (KR)

( * ) Notice: Subject to any disclaimer, the term of this patent is extended or adjusted under 35 U.S.C. 154(b) by 0 days.

(21) Appl. No.: 18/558,164

(22) PCT Filed: Mar. 15, 2022

(86) PCT No.: PCT/KR2022/003582
§ 371 (c)(1),
(2) Date: Oct. 30, 2023

(87) PCT Pub. No.: WO2023/033281
PCT Pub. Date: Mar. 9, 2023

(65) Prior Publication Data
US 2024/0266006 A1 Aug. 8, 2024

(30) Foreign Application Priority Data

Aug. 31, 2021 (KR) .................. 10-2021-0115509

(51) Int. Cl.
G16C 20/30 (2019.01)
G16C 20/40 (2019.01)

(52) U.S. Cl.
CPC ............ *G16C 20/30* (2019.02); *G16C 20/40* (2019.02)

(58) Field of Classification Search
None
See application file for complete search history.

(56) References Cited

FOREIGN PATENT DOCUMENTS

| CN | 112037856 A | 12/2020 |
|---|---|---|
| KR | 1020200017653 A | 2/2020 |
| KR | 1020200126720 A | 11/2020 |
| KR | 102213670 B1 | 2/2021 |
| KR | 102237189 B1 | 4/2021 |

OTHER PUBLICATIONS

A. F. T. Martins et al., "From Softmax to Sparsemax: A Sparse Model of Attention and Multi-Label Classification," Proceedings of the 33rd International Conference on Machine Learning, vol. 48 (2016).
K. Koyama et al., Cross Attention DTI: Drug-Target Interaction Prediction with Cross Attention module in the Blind Evaluation Setup, BIOKDD (Aug. 24, 2020).
Y. Zeng et al., "Deep drug-target binding affinity prediction with multiple attention blocks," Brief. Bioinformatics,2021; vol. 22(5).

*Primary Examiner* — Walter L Lindsay, Jr.
*Assistant Examiner* — Geoffrey T Evans
(74) *Attorney, Agent, or Firm* — Umberg Zipser LLP

(57) ABSTRACT

Disclosed is a method for predicting an affinity between a drug and a target substance, which is performed by a computing device including at least one processor according to some embodiments of the present disclosure. The method for predicting an affinity between a drug and a target substance may include: extracting a feature value of each of the drug and the target substance by using a first neural network; performing a cross attention between the feature values by using a second neural network; and predicting the affinity between the drug and the target substance based on a result of performing the cross attention by using a third neural network.

11 Claims, 7 Drawing Sheets

METHOD FOR PREDICT AFFINITY BETWEEN DRUG AND TARGET SUBSTANCE

TECHNICAL FIELD

The present disclosure relates to a method for predicting the affinity between a drug and a target substance, and particularly, to a method for predicting an affinity by performing a cross attention between a drug and a target substance.

BACKGROUND ART

Recently, various in silico methods are being developed to predict a drug-target interaction (DTI). Here, in silico may be a bioinformatics term meaning computer programming in a virtual experiment. In particular, if whether there is the interaction between a drug and a target substance is carried out based on an actual experiment (in-vitro) (or clinical trial), a lot of time and high cost are consumed, so many researchers may prefer predicting the interaction between the drug and the target substance through an in silico-based virtual experiment.

As one of the technologies for predicting the drug-target interaction, a technology that predicts an affinity between the drug and the target, based on graph convolutional networks, "GraphDTA: prediction of drug-target binding affinity using graph convolutional networks" is known in the related art. However, since the technology lacks consideration for interpretability of prediction results and interactions between drugs and target substances, there may be limits to the reliability of the results.

DISCLOSURE

Technical Problem

The present disclosure is contrived in response the above-described background art, and has been made in an effort to provide a method for predicting an affinity by performing a cross attention between a drug and a target substance.

Technical objects of the present disclosure are not restricted to the technical object mentioned as above. Other unmentioned technical objects will be apparently appreciated by those skilled in the art by referencing to the following description.

Technical Solution

In order to solve the problem, disclosed is a method for predicting an affinity between a drug and a target substance, the method performed by a computing device including at least one processor. The method for predicting an affinity between a drug and a target substance may include: extracting a feature value of each of the drug and the target substance by using a first neural network; performing a cross attention between the feature values by using a second neural network; and predicting the affinity between the drug and the target substance based on a result of performing the cross attention by using a third neural network.

Further, the extracting of the feature values of each of the drug and the target substance by using the first neural network may include: extracting the feature value of the drug by using a first sub network included in the first neural network; and extracting the feature value of the target substance by using a second sub network included in the first neural network.

Further, the performing of the cross attention between the feature values by using the second neural network may include: calculating a feature value of the target substance for the drug by performing a cross attention which aligns the feature value of the drug and the feature value of the target substance based on a first sub network included in the second neural network; and calculating a feature value of the drug for the target substance by performing the cross attention which aligns the feature value of the drug and the feature value of the target substance based on a second sub network included in the second neural network.

Further, the calculating of the feature value of the target substance for the drug by performing the cross attention which aligns the feature value of the drug and the feature value of the target substance based on the first sub network included in the second neural network may include: generating a first key and a first value for the drug based on the feature value of the drug, and generating a second query for the target substance based on the feature value of the target substance; generating a cross attention vector based on the second query and the first key; and calculating the feature value of the target substance for the drug by applying the cross attention vector to the first value.

Further, the generating of the cross attention vector based on the second query and the first key may include: generating the cross attention vector by calculating a probability value which is based on the second query and the first key for an entire sequence of the target substance.

Further, the probability value may be determined based on a sparsemax function.

Further, the calculating of the feature value of the target substance for the drug by applying the cross attention vector to the first value may include: performing an element-wise operation between the cross attention vector and the first value; and calculating the feature value of the target substance for the drug based on a result of performing the element-wise operation.

Further, the calculating of the feature value of the drug for the target substance by performing the cross attention which aligns the feature value of the drug and the feature value of the target substance based on the second sub network included in the second neural network may include: generating a second key and a second value for the target substance based on the feature value of the target substance, and generating a first query for the drug based on the feature value of the drug; generating the cross attention vector based on the first query and the second key; and calculating the feature value of the drug for the target substance by applying the cross attention vector to the second value.

Further, the generating of the cross attention vector based on the first query and the second key may include: generating the cross attention vector by calculating a probability value which is based on the first query and the second key for an entire sequence of the drug.

Further, the probability value may be determined based on the sparsemax function.

Further, the calculating of the feature value of the drug for the target substance by applying the cross attention vector to the second value may include: performing the element-wise operation between the cross attention vector and the second value; and calculating the feature value of the drug for the target substance based on the result of performing the element-wise operation.

In a computer program stored in a computer-readable storage medium, the computer program may execute the following methods for predicting an affinity between a drug and a target substance when the computer program is executed by one or more processors, and the method may include: extracting a feature value of each of the drug and the target substance by using a first neural network; performing a cross attention between the feature values by using a second neural network; and predicting the affinity between the drug and the target substance based on a result of performing the cross attention by using a third neural network.

Further, a computing device predicting an affinity between a drug and a target substance may include: a processor including at least one core; and a storage unit storing information related to a drug and a target substance; and the processor is configured to extract a feature value of each of the drug and the target substance by using a first neural network, perform a cross attention between the features by using a second neural network, and predict the affinity between the drug and the target substance based on a result of performing the cross attention by using a third neural network.

Technical solving means which can be obtained in the present disclosure are not limited to the aforementioned solving means and other unmentioned solving means will be clearly understood by those skilled in the art from the following description.

Advantageous Effects

According to some embodiments of the present disclosure, it is possible to provide a method for providing an interpretability of a prediction result and predicting an affinity between a drug and a target substance with high reliability.

Effects which can be obtained in the present disclosure are not limited to the aforementioned effects and other unmentioned effects will be clearly understood by those skilled in the art from the following description.

DESCRIPTION OF DRAWINGS

Various aspects are now described with reference to the drawings and like reference numerals are generally used to designate like elements. In the following embodiments, for the purpose of description, multiple specific detailed matters are presented to provide general understanding of one or more aspects. However, it will be apparent that the aspect(s) can be executed without the specific detailed matters. In other examples, known structures and apparatuses are illustrated in a block diagram form in order to facilitate description of the one or more aspects.

MODE FOR INVENTION

Various embodiments and/or aspects will be now disclosed with reference to drawings. In the following description, for the purpose of a description, multiple detailed matters will be disclosed in order to help comprehensive appreciation of one or more aspects. However, those skilled in the art of the present disclosure will recognize that the aspect(s) can be executed without the detailed matters. In the following disclosure and the accompanying drawings, specific exemplary aspects of one or more aspects will be described in detail. However, the aspects are exemplary and some of various methods in principles of various aspects may be used and the descriptions are intended to include all of the aspects and equivalents thereof. Specifically, in "embodiment", "example", "aspect", "illustration", and the like used in the specification, it may not be construed that a predetermined aspect or design which is described is more excellent or advantageous than other aspects or designs.

Hereinafter, like reference numerals refer to like or similar elements regardless of reference numerals and a duplicated description thereof will be omitted. Further, in describing an embodiment disclosed in the present disclosure, a detailed description of related known technologies will be omitted if it is determined that the detailed description makes the gist of the embodiment of the present disclosure unclear. Further, the accompanying drawings are only for easily understanding the embodiment disclosed in this specification and the technical spirit disclosed by this specification is not limited by the accompanying drawings.

Although the terms "first", "second", and the like are used for describing various elements or components, these elements or components are not confined by these terms, of course. These terms are merely used for distinguishing one element or component from another element or component. Therefore, a first element or component to be mentioned below may be a second element or component in a technical spirit of the present disclosure.

Unless otherwise defined, all terms (including technical and scientific terms) used in the present specification may be used as the meaning which may be commonly understood by the person with ordinary skill in the art, to which the present disclosure pertains. Terms defined in commonly used dictionaries should not be interpreted in an idealized or excessive sense unless expressly and specifically defined.

Further, the terms "information" and "data" used in the specification may also be often used to be exchanged with each other.

It should be appreciated that the term "comprise" and/or "comprising" means presence of corresponding features and/or components. However, it should be appreciated that the term "comprises" and/or "comprising" means that presence or addition of one or more other features, components, and/or a group thereof is not excluded. Further, when not separately specified or it is not clear in terms of the context that a singular form is indicated, it should be construed that the singular form generally means "one or more" in this specification and the claims.

Further, the terms "information" and "data" used in the specification may also be often used to be exchanged with each other.

It should be understood that, when it is described that a component is "connected to" or "accesses" another component, the component may be directly connected to or access the other component or a third component may be present therebetween. In contrast, it should be understood that, when it is described that a component is "directly connected to" or "directly access" another component, no component is present between the component and the other component.

Suffixes "module" and "unit" for components used in the following description are given or mixed in consideration of easy preparation of the specification only and do not have their own distinguished meanings or roles.

The objects and effects of the present disclosure, and technical constitutions of accomplishing these will become obvious with reference to embodiments to be described below in detail along with the accompanying drawings. In describing the present disclosure, a detailed description of known function or constitutions will be omitted if it is determined that it unnecessarily makes the gist of the present disclosure unclear. In addition, terms to be described below as terms which are defined in consideration of functions in the present disclosure may vary depending on the intention or a usual practice of a user or an operator.

However, the present disclosure is not limited to embodiments disclosed below but may be implemented in various different forms. However, the embodiments are provided to make the present disclosure be complete and completely announce the scope of the present disclosure to those skilled in the art to which the present disclosure belongs and the present disclosure is just defined by the scope of the claims. Accordingly, the terms need to be defined based on contents throughout this specification.

In the present disclosure, a computing device may predict an affinity between a drug and a target substance. Here, the affinity may represent binding force or force acting between the drug and the target substance. The target substance may be, for example, a protein or the like. The computing device may extract a feature value of each of the drug and the target substance by using a neural network to predict the affinity. When the feature value is extracted, the computing device may perform a gated cross attention between the feature values, and predict the affinity between the drug and the target substance based on a result of performing the cross attention. Here, the attention may be a technique that allows a deep learning model to pay attention to a specific vector to increase a performance of a model. In the present disclosure, the cross attention between the feature values of the drug and the target substance is performed based on the attention technique to predict an affinity with a higher reliability. Hereinafter, a method for predicting, by a computing device, an affinity between a drug and a target substance according to the present disclosure will be described with reference to FIGS. 1 to 7.

Figure 1:
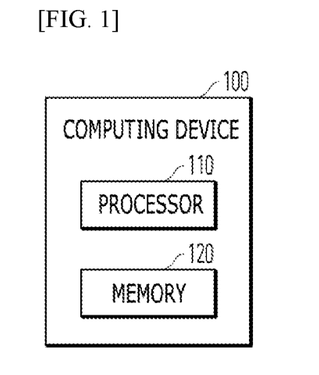
FIG. 1 is a block diagram for describing an example of a computing device according to some embodiments of the present disclosure.

FIG. 1 is a block diagram for describing an example of a computing device according to some embodiments of the present disclosure.

Referring to FIG. 1, the computing device 100 may include a processor 110 and a storage unit 120. However, components described above are not particularly required in implementing the computing device 100, so the computing device 100 may have components more or less than components listed above.

The computing device 100 may include a predetermined type computer system or computer device such as a microprocessor, a main frame computer, a digital processor, a portable device, or a device controller.

The processor 110 may generally process an overall operation of the computing device 100. The processor 110 processes a signal, data, information, and the like input or output through the components included in the computing device 100 or drives the application program stored in the storage unit 120 to provide or process information or a function appropriate for the user.

In the present disclosure, the processor 110 may extract a feature value of each of a drug and a target substance. As an example, the processor 110 may extract the feature value of each of the drug and the target substance by using a first neural network. Here, the first neural network may be convolutional neural networks (CNN) in the related art. Alternatively, the first neural network may also be a feature value extractor for extracting the feature value of each of the drug and the target substance. When the feature values are extracted, the processor 110 may perform a gated cross attention between the features by using a second neural network. In the present disclosure, the cross attention may be an attention that calculates a feature value of the target substance for the drug by aligning the feature value of the drug and the feature value of the target substance. Alternatively, the cross attention may be an attention that calculates a feature value of the drug for the target substance by aligning the feature value of the drug and the feature value of the target substance. As an example, the processor 110 may generate a cross attention vector based on a key for the drug and a query for the target substance in order to calculate the feature value of the target substance for the drug. Here, the cross attention vector may be a gating function for calculating the feature value of the target substance for the drug. The processor 110 may calculate the feature value of the target substance for the drug by applying the cross attention vector to a value for the drug. In other words, the processor 110 may alternately use the feature value of the target substance as well as the feature value of the drug in calculating the feature value of the target substance for the drug. The processor 110 may predict the affinity between the drug and the target substance by using a third neural network when the feature value of the target substance for the drug is calculated and the feature value of the drug for the target substance is calculated. Therefore, the processor 110 may predict the affinity between the drug and the target substance with higher reliability. Hereinafter, an example of predicting, by the processor 110, the affinity between the drug and the target substance according to the present disclosure will be described through FIGS. 2 to 5.

the memory 120 may include memory and/or non-transitory storage medium. the memory 120 may include at least one type of storage medium of a flash memory type storage medium, a hard disk type storage medium, a multimedia card micro type storage medium, a card type memory (for example, an SD or XD memory, or the like), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk.

In the present disclosure, the storage unit 120 may store information related to a plurality of drugs and a plurality of target substances as a database. As an example, the storage unit 120 may store raw data of drug candidate compounds represented by a simplified molecular input line entry system (SMILES). Here, SMILES may be a line notation standard for describing the structure of a chemical species using a short ASCII character string. As an example, the storage unit 120 may store raw data of drug candidate compounds received from a ZINC database, which is a free database for chemicals available through a communication unit (not illustrated). In addition, the storage unit 120 may store amino acid sequence data representing the sequence of amino acids that are members of proteins.

According to the configuration described above, the computing device 100 may use the feature value of the target substance in calculating the feature value of the target substance for the drug. Further, the computing device 100 may use the feature value of the drug in calculating the feature value of the drug for the target substance. The computing device 100 may predict the affinity between the drug and the target substance based on the calculated feature value of the target substance for the drug and the calculated feature value of the drug for the target substance. Therefore, the computing device 100 may predict the affinity between the drug and the target substance with higher reliability. Hereinafter, a specific method for predicting, by the computing device 100, the affinity between the drug and the target substance according to the present disclosure will be described with reference to FIG. 2.

Figure 2:
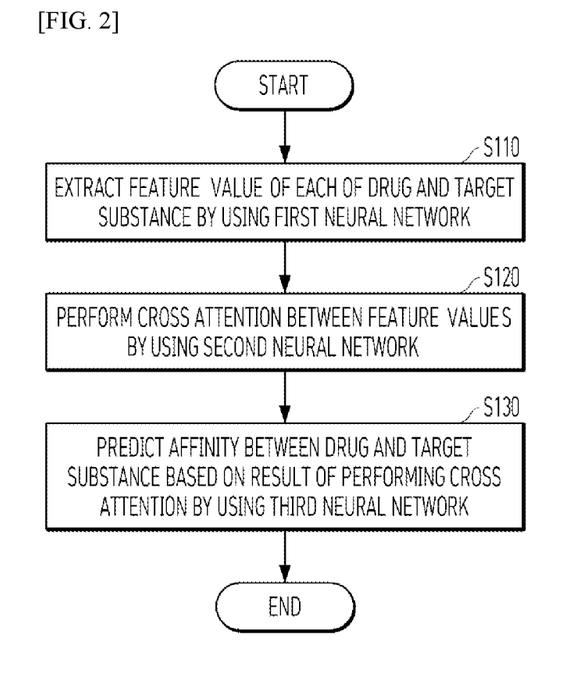
FIG. 2 is a flowchart for describing an example of a method for predicting, by a computing device, an affinity between a drug and a target substance according to some embodiments of the present disclosure.

FIG. 2 is a flowchart for describing an example of a method for predicting, by a computing device, an affinity between a drug and a target substance according to some embodiments of the present disclosure.

Referring to FIG. 2, the processor 110 of the computing device 100 may extract the feature value of each of the drug and the target substance by using the first neural network (S110).

As an example, the processor 110 may extract the feature value of the drug by using a first sub network included in the first neural network. Here, each of the first neural network and the first sub network may be convolutional neural networks (CNN), but is not limited thereto, and may also adopt a network model such as an artificial neural network (ANN), a deep neural network (DNN), or a recurrent neural network (RNN). The processor 110 may extract the feature value from the drug stored in the storage unit 120 by using the first sub network. As an example, the processor may extract and determine the feature value of the drug through the following equation.

$$r_d = \text{pooling}(d_{1:n_d}) \quad \text{[Equation 1]}$$

Here, pooling(•) may be global max pooling or average pooling. $n_d$ may represent a sequence length of the feature value of the drug and subscript 1 may represent a sequential range of the feature value of the drug.

The processor 110 may extract the feature value of the target substance by using a second sub network included in the first neural network. Here, the second sub network may be a convolutional neural network, but is not limited thereto, and a network model such as an ANN, DNN, or RNN may be used. The processor 110 may extract the feature value from the target substance stored in the storage unit 120 by using the second sub network. As an example, the processor may extract and determine the feature value of the target substance through the following equation.

$$r_p = \text{pooling}(p_{1:n_p}) \quad \text{[Equation 2]}$$

Here, pooling(•) may be the global max pooling or average pooling. $n_p$ may represent the sequence length of the feature value of the target substance and subscript 1 may represent the sequential range of the feature value of the target substance.

The processor 110 of the computing device 100 may perform a gated cross attention between the feature values by using the second neural network (S120). Here, performing the gated cross attention may be an operation of calculating the feature value of the target substance for the drug by aligning the feature value of the drug and the feature value of the target substance. Alternatively, performing the gated cross attention may be an operation of calculating the feature value of the drug for the target substance by aligning the feature value of the drug and the feature value of the target substance.

As an example, the processor 110 performs the gated cross attention between the feature value of the drug and the feature value of the target substance based on the first sub network included in the second neural network to calculate the feature value of the target substance for the drug. Specifically, the processor 110 may generate a first key and a first value for the drug based on the feature value of the drug extracted by using the first neural network. The processor 110 may generate a second query for the target substance based on the feature value of the target substance extracted by using the first neural network. The processor 110 generates a gated cross attention vector based on the second query and the first key, and applies the generated gated cross attention vector to the first value to calculate the feature value of the target substance for the drug. Here, the gated cross attention vector may be a gating function for calculating the feature value of the target substance for the drug.

The processor 110 performs the gated cross attention between the feature value of the drug and the feature value of the target substance based on the second sub network included in the second neural network to calculate the feature value of the drug for the target substance. Specifically, the processor 110 may generate a second key and a second value for the target substance based on the feature value of the drug extracted by using the first neural network. The processor 110 may generate a first query for the drug based on the feature value of the drug extracted by using the first neural network. The processor 110 generates the gated cross attention vector based on the first query and the second key, and applies the generated gated cross attention vector to the second value to calculate the feature value of the drug for the target substance. Hereinafter, a method for calculating, by the processor 110, the feature value of the target substance for the drug according to the present disclosure will be described through FIGS. 3 and 4. Further, a method for calculating, by the processor 110, the feature value of the drug for the target substance according to the present disclosure will be described through FIGS. 3 and 5.

According to some embodiments of the present disclosure, the processor 110 of the computing device 100 may define a result of performing the gated cross attention of the target substance for the drug through the following equation.

$$d'_{1:n_d} = g_{p \to d}(d_{1:n_d}, p_{1:n_p}; \theta_{p \to d})$$ [Equation 3]

Here, g(•) may represent an attention function considering relative information (target substance information). For example, $g_{p \to d}$ may use a feature value $p_{1:n_p}$ of the target substance in order to reflect an attention based on the target substance to a feature value $d_{1:n_d}$ for the drug by using a learnable parameter $\theta_{p \to d}$ In addition, $g_{p \to d}$ may return $d'_{1:n_d}$ which is an attentioned feature value of $d_{1:n_d}$ by using $p_{1:n_p}$.

Further, the processor 110 of the computing device 100 may define a result of performing the gated cross attention of the drug for the target substance through the following equation.

$$p'_{1:n_p} = g_{d \to p}(p_{1:n_p}, d_{1:n_d}; \theta_{d \to p})$$ [Equation 4]

Here, g(•) may represent the attention function considering relative information (drug information). For example, $g_{d \to p}$ may use a feature value $d_{1:n_d}$ of the target substance in order to reflect an attention based on the drug to a feature value $pd_{1:n_p}$ for the target substance by using a learnable parameter $\theta_{d \to p}$. In addition, $g_{p \to d}$ may return $p'_{1:n_p}$ which is an attentioned feature of $p_{1:n_p}$ by using $d_{1:n_d}$.

According to some embodiments of the present disclosure, the gated cross attention may also be a multi-head attention or a multi-head gated attention. Here, the multi-head attention may be an attention that performs a plurality of gated cross attentions in parallel to calculate the feature value of the target substance for the drug and the feature value of the drug for the target substance.

The processor 110 of the computing device 100 may predict the affinity between the drug and the target substance based on a result of performing the gated cross attention by using a third neural network (S130).

In some embodiments, an interaction between the drug and the target substance for which the processor 110 performs the gated cross attention may be explicitly configured. For example, the processor 110 may generate an attention map as a result of an explicit interaction. The attention map may serve as an interpretable element for a prediction result, and the processor 110 may predict the affinity between the drug and the target substance by using the attention map.

According to some embodiments of the present disclosure, the processor 110 of the computing device 100 may generate a score for the predicted affinity. As an example, the processor 110 may generate the score through the following equation.

$$\hat{y} = \phi(r_d, r_p; \theta_i)$$ [Equation 5]

Here, ŷ may represent an affinity score. φ(•) may represent the third neural network and $\theta_i$ may represent a parameter used by the third neural network.

According to the above-described configuration, the computing device 100 may predict the affinity between the drug and the target substance based on the gated cross attention. As an example, the processor 110 may calculate the feature value of the target substance for the drug by performing the gated cross attention of aligning the feature value of the drug and the feature value of the target substance. Further, the processor 110 may calculate the feature value of the drug for the target substance by performing the gated cross attention of aligning the feature value of the drug and the feature value of the target substance. Since the processor 110 considers relative information in calculating the feature value for each of the drug and the target substance, the processor 110 may predict the affinity with higher reliability. Hereinafter, a method for performing, by the processor 110 of the computing device 100, the gated cross attention between the feature values by using the second neural network will be described.

Figure 3:
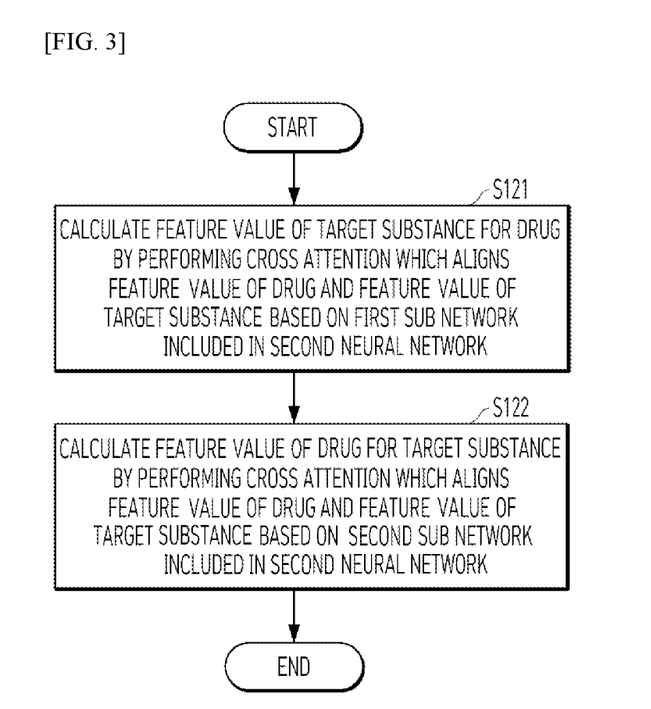
FIG. 3 is a flowchart for describing an example of a method for performing, the computing device, a cross attention between feature values according to some embodiments of the present disclosure.
Figure 4:
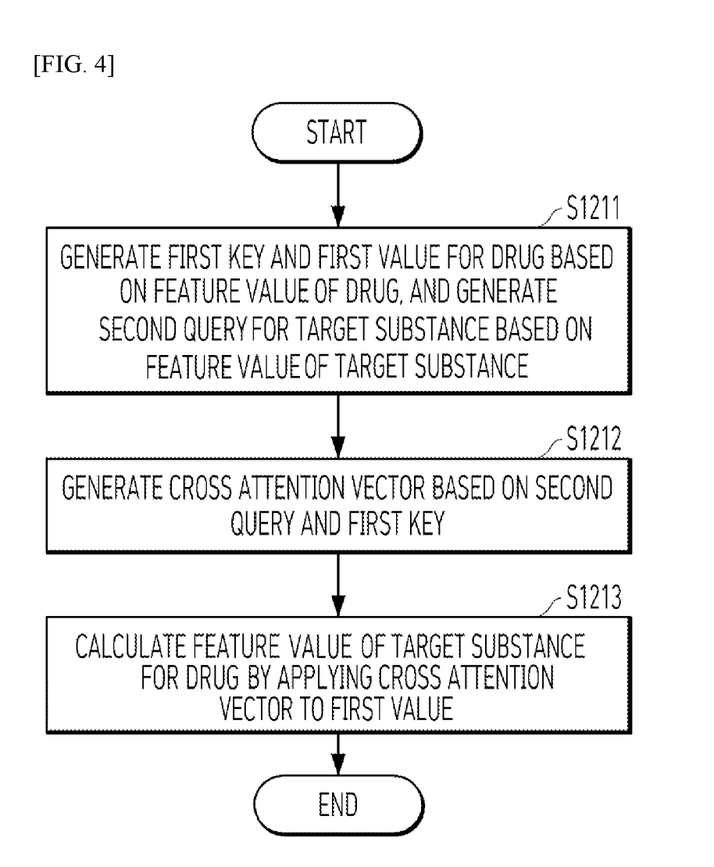
FIG. 4 is a flowchart for describing an example of a method for calculating, by the computing device, a feature value of the target substance for the drug according to some embodiments of the present disclosure.
Figure 5:
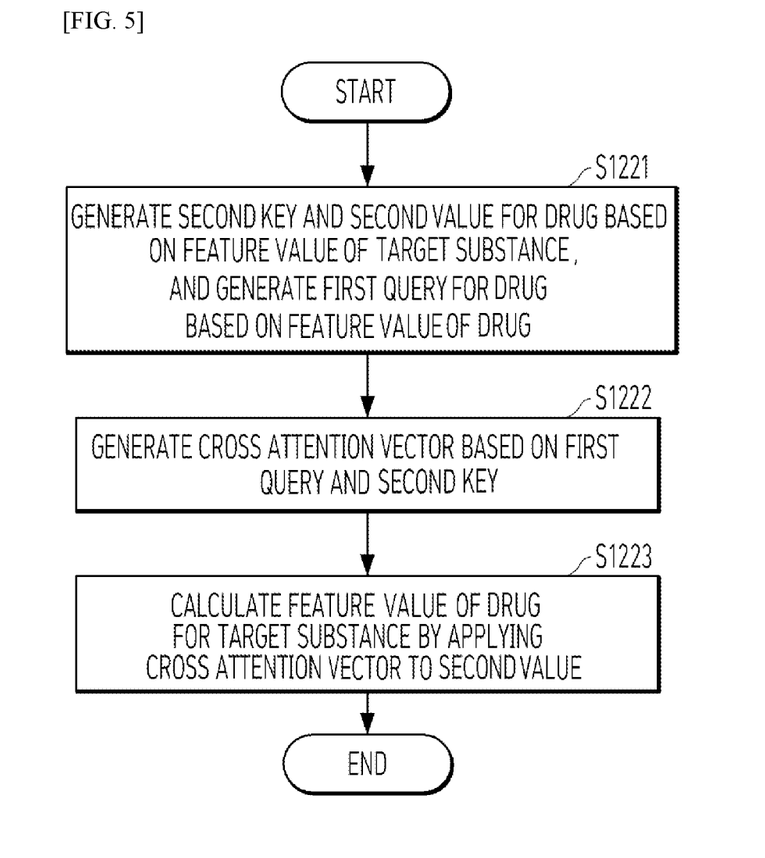
FIG. 5 is a flowchart for describing an example of a method for calculating, by the computing device, a feature value of the drug for the target substance according to some embodiments of the present disclosure.

FIG. 3 is a flowchart for describing an example of a method for performing, the computing device, a cross attention between feature values according to some embodiments of the present disclosure. FIG. 4 is a flowchart for describing an example of a method for calculating, by the computing device, a feature value of the target substance for the drug according to some embodiments of the present disclosure. FIG. 5 is a flowchart for describing an example of a method for calculating, by the computing device, a feature value of the drug for the target substance according to some embodiments of the present disclosure.

Referring to FIG. 3, the processor 110 of the computing device 100 may perform the gated cross attention of aligning the feature value of the drug and the feature value of the target substance based on the first sub network included in the second neural network. In addition, the processor 110 may calculate the feature value of the target substance for the drug based on a result of performing the gated cross attention (S121).

Specifically, referring to FIG. 4, the processor 110 may generate a first key and a first value for the drug based on the feature value of the drug extracted by using the first sub network included in the first neural network. The processor 110 may generate a second query for the target substance based on the feature value of the target substance extracted by using the second sub network included in the first neural network. More specifically, the processor 110 converts the same input $d_{1:n_d}$ into a weight matrices $W_K$ and $W_V$ to configure the first key and the first value. Here, $n_d$ may represent a sequence length of the feature value of the drug and subscript 1 may represent a sequential range of the feature value of the drug. The processor 110 may represent the generated weight matrices as $K_d$ and $V_d$, respectively, and $K_d$ $V_d$ may have the same dimension as the input $d_{1:n_d}$. The processor 110 converts the same input $p_{1:n_p}$ into a weight matrix $W_Q$ to configure a second query. Here, $n_p$ may represent a sequence length of the feature value of the target substance (protein) and subscript 1 may represent a sequential range of the feature value of the target substance. The processor 110 may represent the generated weight matrix as $Q_p$, and $Q_p$ may have the same dimension as the input $d_{1:n_d}$.

The processor 110 may generate the gated cross attention vector based on the second query and the first key (S1212).

Specifically, the processor 110 may generate the gated cross attention vector by calculating a probability value which is based on the second query and the first key for an entire sequence of the target substance. In other words, the processor 110 may generate a context-level gated cross attention vector by performing a context-level attention for the entire sequence instead of a token-level attention.

As an example, the processor 110 may generate the gated cross attention vector of the target substance for the drug through the following equation.

$$a = \frac{1}{n_p}\sum_{i=1}^{n_p} softmax\left(\frac{Q_p K_d^T}{\sqrt{b}}\right)_{:,i} \qquad \text{[Equation 6]}$$

Here, a may represent the gated cross attention vector of the target substance for the drug. $n_p$ may represent a sequential length of the feature value of the target substance. softmax may represent a function of performing normalization for an output value. b may represent a dimension of the feature value of the drug. $K_d$ may represent the first key and $Q_p$ may represent the second query.

According to some embodiments of the present disclosure, the probability value may be determined based on a sparsemax function. In some embodiments, the gated cross attention vector may calculate a probability value for the entire sequence. Most of the sequence probability values are not 0, but have small values, so an attention to important sequences may be weakened. Therefore, in the present disclosure, an attention vector may be sparsely generated so that the second neural network may perform the attention on the important sequence. To this end, the processor 110 may determine the probability value by using the sparsemax function instead of the SoftMax function. Here, the sparsemax function is a function that generates values such that most of the values of the matrix are 0, and may be a function for considering small weights to be insignificant. Therefore, the processor 110 may generate the gated cross attention vector of the target substance for the drug through the following equation by using the sparsemax function.

$$a = \frac{1}{n_p}\sum_{i=1}^{n_p} sparsemax\left(\frac{Q_p K_d^T}{\sqrt{b}}\right)_{:,i} \qquad \text{[Equation 7]}$$

The processor 110 may calculate the feature value of the target substance for the drug by applying the generated gated cross attention vector to the first value (S1213).

Specifically, the processor 110 may perform an element-wise operation between the gated cross attention vector and the first value. Here, the element-wise operation may be a method of performing an operation in a broadcasting scheme when dimensions do not match. As an example, the element-wise operation may adopt library Numpy of Python capable of processing a matrix or a multi-dimensional array. However, the present disclosure is not limited thereto. The processor 110 may calculate the feature value of the target substance for the drug based on the result of performing the element-wise operation. As an example, the processor 110 may calculate the feature value of the target substance for the drug by performing the element-wise operation between the gated cross attention vector and the first value through the following equation.

$$V'_d = softmax(a) \odot V_d \qquad \text{[Equation 8]}$$

Here, $V_d$ may represent the feature value of the target substance for the drug. a may represent the gated cross attention vector. In addition, $\odot$ may represent a symbol representing the element-wise operation and $V_d$ may represent the first value.

According to some embodiments of the present disclosure, the processor 110 may determine the feature value of the target substance for the drug by using the sparsemax function instead of the SoftMax function so that the second neural network may sparsely generate the attention map. Therefore, the processor 110 may calculate the feature value of the target substance for the drug through the following equation by using the sparsemax function.

$$V'_d = sparsemax(a) \odot V_d \qquad \text{[Equation 9]}$$

Through the above-described process, the processor 110 of the computing device 100 may perform the gated cross attention of aligning the feature value of the drug and the feature value of the target substance based on the first sub network included in the second neural network. In addition, the processor 110 may calculate the feature value of the target substance for the drug based on a result of performing the gated cross attention.

Meanwhile, referring back to FIG. 3, the processor 110 of the computing device 100 may perform the gated cross attention of aligning the feature value of the drug and the feature value of the target substance based on the second sub network included in the second neural network. In addition, the processor 110 may calculate the feature value of the drug for the target substance based on the result of performing the gated cross attention (S122).

Specifically, referring to FIG. 5, the processor 110 may generate a second key and a second value for the target substance based on the feature value of the target substance extracted by using the second sub network included in the first neural network. In addition, the processor 110 may generate a first query for the drug based on the feature value of the drug extracted by using the first sub network included in the first neural network (S1221). More specifically, the processor 110 converts the same input $p_{1:n_p}$ into weight matrices and $W_K$ and $W_V$ to configure the second key and the second value. Here, $n_p$ may represent the sequence length of the feature value of the target substance and subscript 1 may represent the sequential range of the feature value of the target substance. The processor 110 may represent the generated weight matrices as $K_p$ and $V_p$, respectively, and $K_p$ and $V_p$ may have the same dimension as the input $p_{1:n_p}$. The processor 110 converts the same input $d_{1:n_d}$ into a weight matrix $W_Q$ to configure a second query. Here, $n_d$ may represent a sequence length of the feature value of the drug and subscript 1 may represent a sequential range of the feature value of the drug. The processor 110 may represent the generated weight matrix as $Q_d$, and $Q_d$ may have the same dimension as the input $p_{1:n_p}$.

The processor 110 may generate the gated cross attention vector based on the first query and the second key (S1212).

Specifically, the processor 110 may generate the gated cross attention vector by calculating a probability value which is based on the first query and the second key for an entire sequence of the drug. In other words, the processor 110 may generate a context-level gated cross attention vector by performing a context-level attention for the entire sequence instead of a token-level attention.

As an example, the processor 110 may generate the gated cross attention vector of the drug for the target substance through the following equation.

$$a = \frac{1}{n_d}\sum_{i=1}^{n_d} softmax\left(\frac{Q_d K_p^T}{\sqrt{b}}\right)_{:,i} \qquad \text{[Equation 10]}$$

Here, a may represent the gated cross attention vector of the drug for the target substance. $n_d$ may represent a sequential length of the feature value of the drug. softmax may represent a function of performing normalization for an output value. b may represent a dimension of the feature value of the target substance. $K_p$ may represent the second key and $Q_d$ may represent the first query.

According to some embodiments of the present disclosure, the probability value may be determined based on a sparsemax function. In some embodiments, the processor 110 may generate the gated cross attention vector of the drug for the target substance through the following equation by using the sparsemax function.

$$a = \frac{1}{n_d} \sum_{i=1}^{n_d} sparsemax\left(\frac{Q_d K_p^T}{\sqrt{b}}\right)_{:,i} \quad \text{[Equation 11]}$$

The processor 110 may calculate the feature value of the drug for the target substance by applying the generated gated cross attention vector to the second value (S1223).

Specifically, the processor 110 may perform an element-wise operation between the gated cross attention vector and the second value. For example, the processor 110 may perform an element-wise operation using Numpy, a Python library capable of processing matrices or multidimensional arrays. However, the present disclosure is not limited thereto. The processor 110 may calculate the feature value of the drug for the target substance based on the result of performing the element-wise operation. As an example, the processor 110 may calculate the feature value of the drug for the target substance by performing the element-wise operation between the gated cross attention vector and the second value through the following equation.

$$V'_p = softmax(a) \odot V_p \quad \text{[Equation 12]}$$

Here, $V'_p$ may represent the feature value of the drug for the target substance. a may represent the gated cross attention vector. In addition, $\odot$ may represent the symbol representing the element-wise operation and $V_p$ may represent the second value.

According to some embodiments of the present disclosure, the processor 110 may determine the feature value of the target substance for the drug by using the sparsemax function instead of the SoftMax function so that the second neural network may sparsely generate the attention map. Therefore, the processor 110 may calculate the feature value of the drug for the target substance through the following equation by using the sparsemax function.

$$V'_p = sparsemax(a) \odot V_p \quad \text{[Equation 13]}$$

Through the above-described process, the processor 110 of the computing device 100 may perform the gated cross attention of aligning the feature value of the drug and the feature value of the target substance based on the second sub network included in the second neural network. In addition, the processor 110 may calculate the feature value of the drug for the target substance based on the result of performing the gated cross attention.

Hereinafter, a specific framework for implementing the method for predicting affinity between the drug and the target substance according to the present disclosure will be described.

Figure 6:
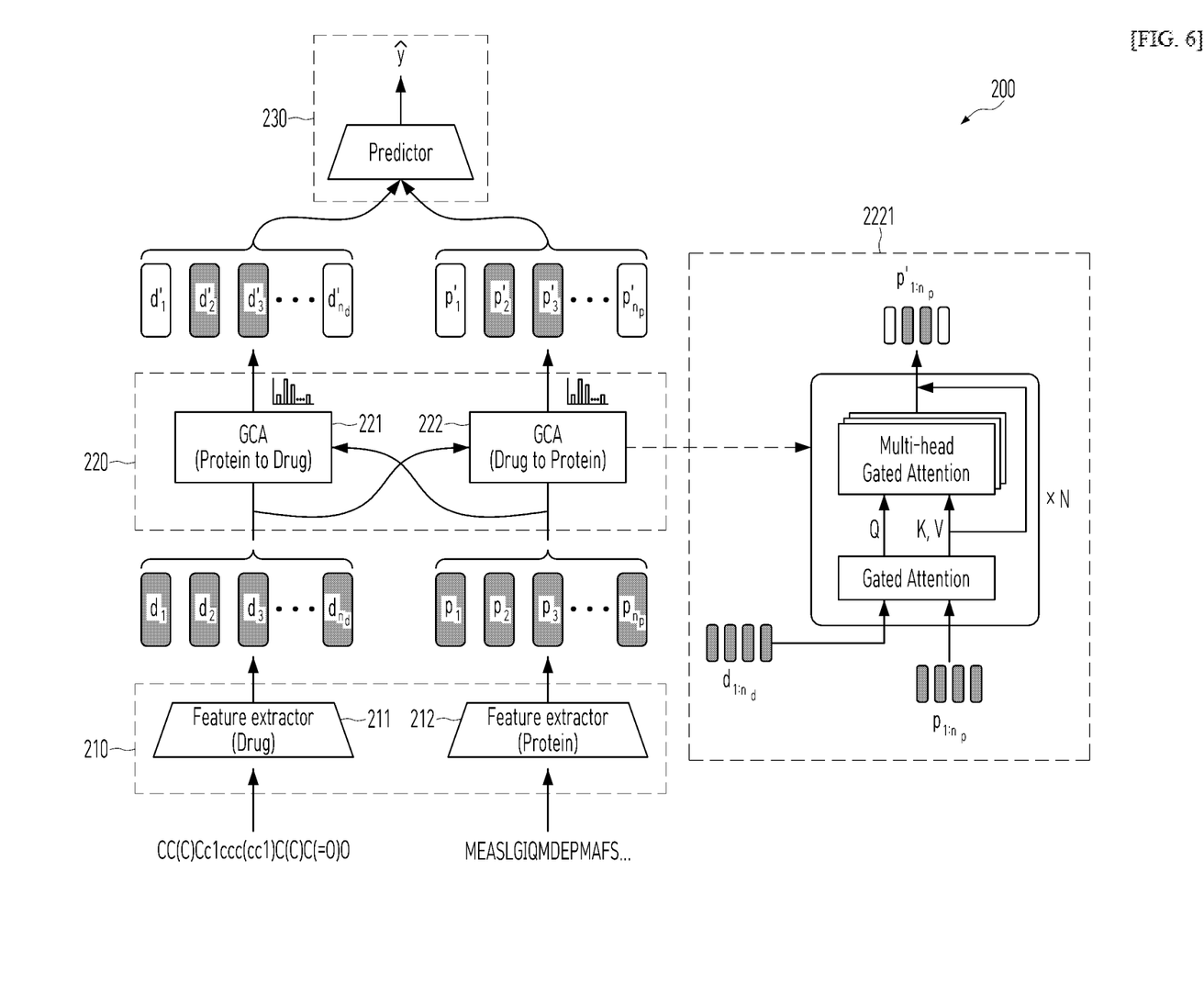
FIG. 6 is a diagram for describing an example of a framework for implementing a method for predicting an affinity between a drug and a target substance according to some embodiments of the present disclosure.

FIG. 6 is a diagram for describing an example of a framework for implementing a method for predicting an affinity between a drug and a target substance according to some embodiments of the present disclosure.

Referring to FIG. 6, the framework 200 for implementing the method for predicting the affinity between the drug and the target substance may include a first neural network 210, a second neural network 220, and a third neural network 230. However, the present disclosure is not limited thereto.

In some embodiment, the first neural network 210 may include a first sub network 211 and a second sub network 212. In addition, the processor 110 may extract a feature value of the drug (e.g., $d_1, d_2, d_3 \bullet \bullet \bullet d_{n_d}$) by using the first sub network 211 and extract a feature value of the target substance (e.g., $p_1, p_2, p_3 \bullet \bullet \bullet p_{n_p}$) by using a second sub network 212.

The second neural network 220 may include a first sub network 221 and a second sub network 222. In addition, the processor 110 may calculate the feature by aligning the feature of the target substance for the drug (e.g., $d'_1, d'_2, d'_3 \bullet \bullet \bullet d'_{n_d}$) by using the first sub network 221. The processor 110 may calculate the feature (e.g., $p'_1, p'_2, p'_3 \bullet \bullet \bullet p'_{n_p}$) by aligning the feature of the drug for the target substance by using the second sub network 222.

According to some embodiments of the present disclosure, the second neural network 220 may perform multi-head attention 2221. Here, the multi-head attention 2221 may be an attention that performs a plurality of gated cross attentions in parallel to calculate the feature value of the target substance for the drug and the feature value of the drug for the target substance.

The third neural network 230 may predict the affinity between the drug and the target substance based on the result of performing the gated cross attention. Specifically, the processor 110 of the computing device 100 may determine an affinity score ŷ indicating the affinity between the drug and the target substance based on the result of performing the gated cross attention by using the third neural network 230.

Figure 7:
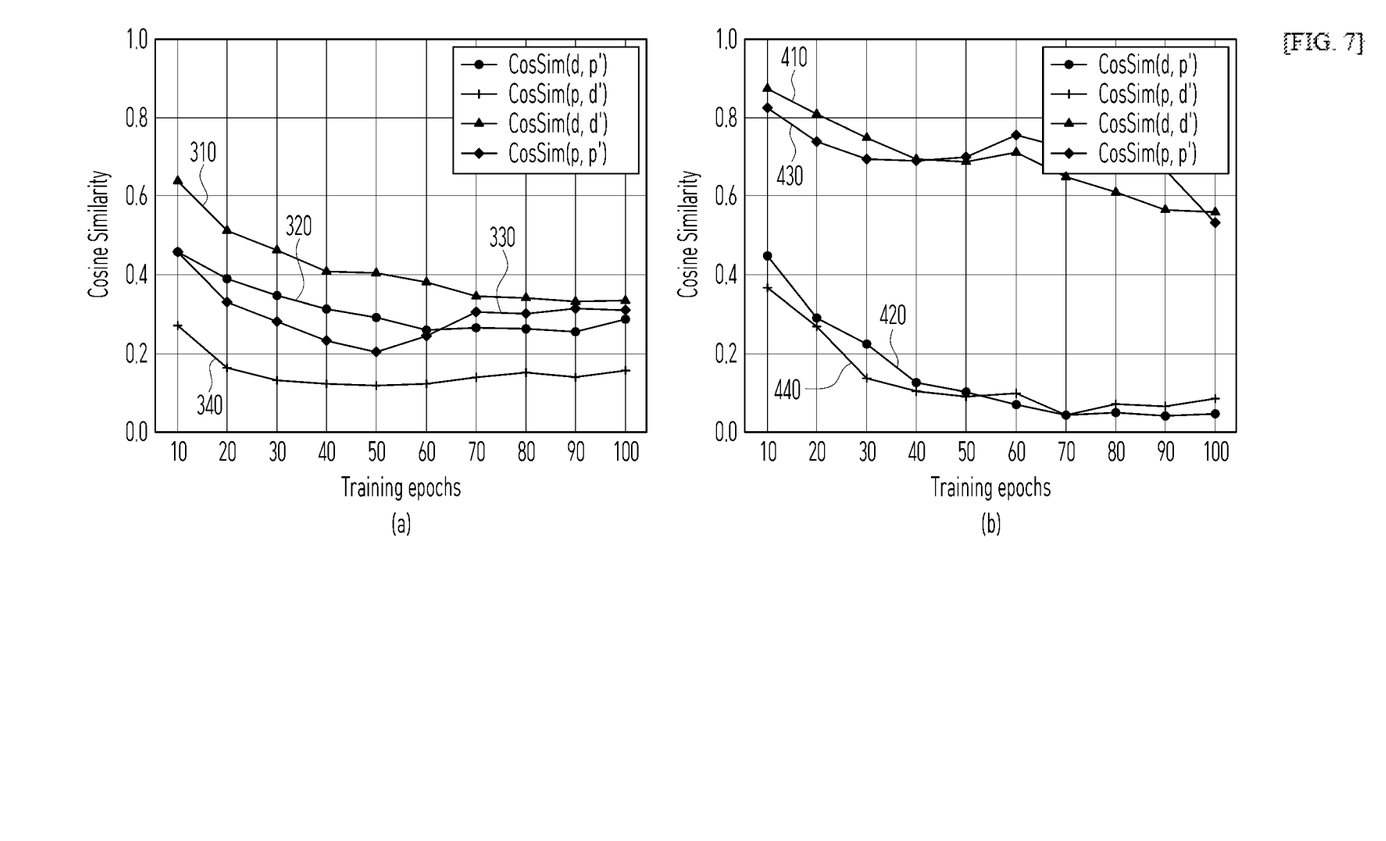
FIG. 7 is a diagram for comparing the present disclosure and related art according to some embodiments of the present disclosure.

A method for predicting a drug-target interaction (DTI) based on deep learning in the related art has shown a promising result in terms of cost. However, in the related art, the interaction between the drug and the target substance may not be considered at the level of the feature value between the drug and the target substance in addition to the interpretability of the prediction result. On the other hand, according to the framework of the present disclosure, the gated cross attention may be performed on the drug and the target substance by constructing an explicit interaction between the drug and the target substance. In addition, the framework according to the present disclosure may calculate probability values for the entire sequence of the drug and the target substance through the gated cross attention vector, which is the gating function for calculating the feature value of the target substance for the drug. In addition, the attention map generated as a result of the explicit interaction may act as an interpretable element. In addition, the framework according to the present disclosure may exhibit a sensitive response to mutations. In other words, the framework according to the present disclosure may also calculate an affinity for a new drug targeting a mutant protein. Hereinafter, a method for predicting the affinity between the drug and the target substance according to the present disclosure through comparison with the related art will be described.

FIG. 7 is a diagram for comparing the present disclosure and related art according to some embodiments of the present disclosure.

FIG. 7(a) may illustrate a result showing a pair-wise similarity between drugs (d, d') and target substances (p, p') using the related art. Here, the related art may be a decoder attention. An x axis of a graph shown in FIG. 7(a) may indicate training epochs and a y axis may indicate a cosine similarity. A first line 310 may indicate the cosine similarity between the drug feature value (d) and the drug feature value (d') aligned by performing the gated cross attention, and a second line 320 may indicate the cosine similarity between the drug feature value and the target substance feature value (p') aligned by performing the gated cross attention. A third line 330 may indicate the cosine similarity between the target substance feature value (p) and the target substance feature value (p') aligned by performing the gated cross attention, and a fourth line 340 may indicate the cosine similarity between the target substance feature value (p) and the drug feature value (d') aligned by performing the gated cross attention. Referring to the first line 310 to the fourth line 340, it can be seen that the first line 310 to the fourth line 340 do not have a large difference in inclination. This may indicate that a distinguishing feature value between a drug and a target substance may not be generated when the attention is performed using the related art.

On the other hand, FIG. 7(b) may illustrate a result showing a pair-wise similarity between the drugs (d, d') and the target substances (p, p') according to the method for predicting the affinity between the drug and the target substance according to the present disclosure. An x axis of a graph shown in FIG. 7(b) may indicate the training epochs and a y axis may indicate the cosine similarity. A first line 410 may indicate the cosine similarity between the drug feature value (d) and the drug feature value (d') aligned by performing the gated cross attention, and a second line 420 may indicate the cosine similarity between the drug feature value (d) and the target substance feature value (p') aligned by performing the gated cross attention. A third line 430 may indicate the cosine similarity between the target substance feature value (p) and the target substance feature value (p') aligned by performing the gated cross attention, and a fourth line 440 may indicate the cosine similarity between the target substance feature value (p) and the drug feature value (d') aligned by performing the gated cross attention. Referring to the first line 410 to the fourth line 440, it can be seen that the first line 410 to the fourth line 440 have a large difference in inclination as compared with the first line 310 to the fourth line 340 shown in FIG. 7(a). This may indicate that a distinguishing feature value between a drug and a target substance is generated when the gated cross attention is performed using the method according to the present disclosure. This may mean that the processor 110 of the computing device 100 may use the distinguishing feature value between the drug and the target substance through the gated cross attention in predicting the affinity between the drug and the target substance by using the third neural network. Accordingly, the affinity predicted by the processor 110 may have high reliability.

Figure 8:
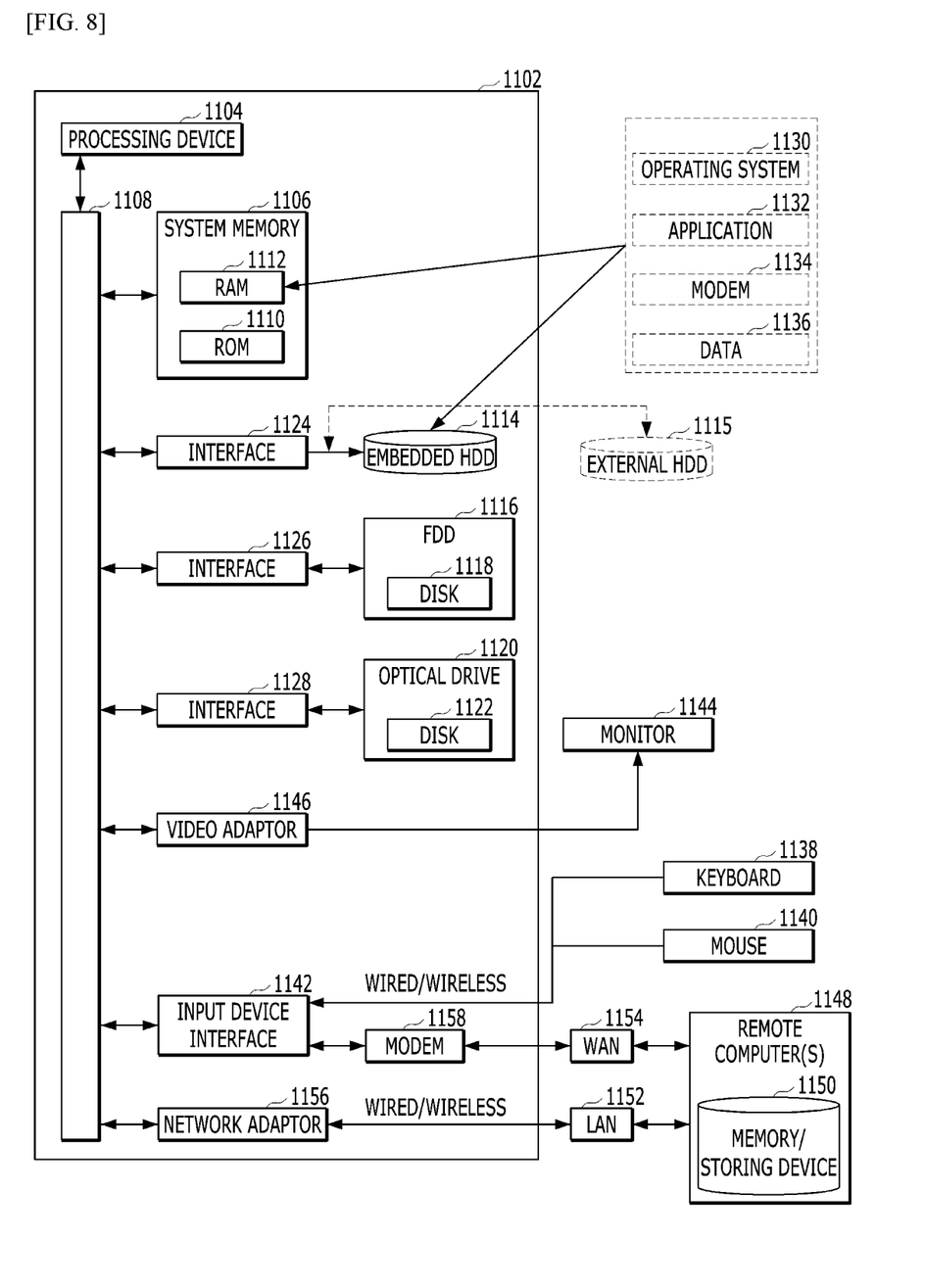
FIG. 8 is a general schematic view of an exemplary computing environment in which embodiments of the present disclosure may be implemented.

FIG. 8 is a normal and schematic view of an exemplary computing environment in which the exemplary embodiments of the present disclosure may be implemented.

The content of this specification has been generally described in relation to computer-executable instructions that can be executed on one or more computers, but those skilled in the art will recognize that the content of this specification may be implemented in combination with other program modules and/or as a combination of hardware and software.

In general, the program module of the present disclosure includes a routine, a procedure, a program, a component, a data structure, and the like that execute a specific task or implement a specific abstract data type. Furthermore, those skilled in the art will recognize that the methods of this disclosure can be implemented in various computer system configurations, including but not limited to single-processor or multiprocessor computer systems, minicomputers, mainframe computers, personal computers, handheld computing devices, microprocessor-based or programmable consumer electronics, and other devices that may be connected to one or more associated devices for operation.

The exemplary embodiments described in the present disclosure may also be implemented in a distributed computing environment in which predetermined tasks are performed by remote processing devices connected through a communication network. In the distributed computing environment, the program module may be positioned in both local and remote memory storage devices.

The computer generally includes various computer readable media. Media accessible by the computer may be computer readable media regardless of types thereof and the computer readable media include volatile and non-volatile media, transitory and non-transitory media, and mobile and non-mobile media. As a non-limiting example, the computer readable media may include both computer readable storage media and computer readable transmission media.

The computer readable storage media include volatile and non-volatile media, transitory and non-transitory media, and mobile and non-mobile media implemented by a predetermined method or technology for storing information such as a computer readable instruction, a data structure, a program module, or other data. The computer readable storage media include a RAM, a ROM, an EEPROM, a flash memory or other memory technologies, a CD-ROM, a digital video disk (DVD) or other optical disk storage devices, a magnetic cassette, a magnetic tape, a magnetic disk storage device or other magnetic storage devices or predetermined other media which may be accessed by the computer or may be used to store desired information, but are not limited thereto.

The computer readable transmission media generally implement the computer readable command, the data structure, the program module, or other data in a carrier wave or a modulated data signal such as other transport mechanism and include all information transfer media. The term "modulated data signal" means a signal acquired by setting or changing at least one of characteristics of the signal so as to encode information in the signal. As a non-limiting example, the computer readable transmission media include wired media such as a wired network or a direct-wired connection and wireless media such as acoustic, RF, infrared and other wireless media. A combination of any media among the aforementioned media is also included in a range of the computer readable transmission media.

An exemplary environment that implements various aspects of the present disclosure including a computer 1102 is shown and the computer 1102 includes a processing device 1104, a system memory 1106, and a system bus 1108. The system bus 1108 connects system components including the system memory 1106 (not limited thereto) to the processing device 1104. The processing device 1104 may be a predetermined processor among various commercial processors. A dual processor and other multi-processor architectures may also be used as the processing device 1104.

The system bus 1108 may be any one of several types of bus structures which may be additionally interconnected to a local bus using any one of a memory bus, a peripheral device bus, and various commercial bus architectures. The system memory 1106 includes a read only memory (ROM) 1110 and a random access memory (RAM) 1112. A basic input/output system (BIOS) is stored in the non-volatile memories 1110 including the ROM, the EPROM, the EEPROM, and the like and the BIOS includes a basic routine that assists in transmitting information among components in the computer 1102 at a time such as in-starting. The RAM 1112 may also include a high-speed RAM including a static RAM for caching data, and the like.

The computer 1102 also includes an interior hard disk drive (HDD) 1114 (for example, EIDE and SATA), in which the interior hard disk drive 1114 may also be configured for an exterior purpose in an appropriate chassis (not illustrated), a magnetic floppy disk drive (FDD) 1116 (for example, for reading from or writing in a mobile diskette 1118), and an optical disk drive 1120 (for example, for reading a CD-ROM disk 1122 or reading from or writing in other high-capacity optical media such as the DVD, and the like). The hard disk drive 1114, the magnetic disk drive 1116, and the optical disk drive 1120 may be connected to the system bus 1108 by a hard disk drive interface 1124, a magnetic disk drive interface 1126, and an optical drive interface 1128, respectively. An interface 1124 for implementing an exterior drive includes at least one of a universal serial bus (USB) and an IEEE 1394 interface technology or both of them.

The drives and the computer readable media associated therewith provide non-volatile storage of the data, the data structure, the computer executable instruction, and others. In the case of the computer 1102, the drives and the media correspond to storing of predetermined data in an appropriate digital format. In the description of the computer readable media, the mobile optical media such as the HDD, the mobile magnetic disk, and the CD or the DVD are mentioned, but it will be well appreciated by those skilled in the art that other types of media readable by the computer such as a zip drive, a magnetic cassette, a flash memory card, a cartridge, and others may also be used in an exemplary operating environment and further, the predetermined media may include computer executable commands for executing the methods of the present disclosure.

Multiple program modules including an operating system 1130, one or more application programs 1132, other program module 1134, and program data 1136 may be stored in the drive and the RAM 1112. All or some of the operating system, the application, the module, and/or the data may also be cached in the RAM 1112. It will be well appreciated that the present disclosure may be implemented in operating systems which are commercially usable or a combination of the operating systems.

A user may input instructions and information in the computer 1102 through one or more wired/wireless input devices, for example, pointing devices such as a keyboard 1138 and a mouse 1140. Other input devices (not illustrated) may include a microphone, an IR remote controller, a joystick, a game pad, a stylus pen, a touch screen, and others. These and other input devices are often connected to the processing device 1104 through an input device interface 1142 connected to the system bus 1108, but may be connected by other interfaces including a parallel port, an IEEE 1394 serial port, a game port, a USB port, an IR interface, and others.

A monitor 1144 or other types of display devices are also connected to the system bus 1108 through interfaces such as a video adapter 1146, and the like. In addition to the monitor 1144, the computer generally includes other peripheral output devices (not illustrated) such as a speaker, a printer, others.

The computer 1102 may operate in a networked environment by using a logical connection to one or more remote computers including remote computer(s) 1148 through wired and/or wireless communication. The remote computer(s) 1148 may be a workstation, a computing device computer, a router, a personal computer, a portable computer, a micro-processor based entertainment apparatus, a peer device, or other general network nodes and generally includes multiple components or all of the components described with respect to the computer 1102, but only a memory storage device 1150 is illustrated for brief description. The illustrated logical connection includes a wired/wireless connection to a local area network (LAN) 1152 and/or a larger network, for example, a wide area network (WAN) 1154. The LAN and WAN networking environments are general environments in offices and companies and facilitate an enterprise-wide computer network such as Intranet, and all of them may be connected to a worldwide computer network, for example, the Internet.

When the computer 1102 is used in the LAN networking environment, the computer 1102 is connected to a local network 1152 through a wired and/or wireless communication network interface or an adapter 1156. The adapter 1156 may facilitate the wired or wireless communication to the LAN 1152 and the LAN 1152 also includes a wireless access point installed therein in order to communicate with the wireless adapter 1156. When the computer 1102 is used in the WAN networking environment, the computer 1102 may include a modem 1158 or has other means that configure communication through the WAN 1154 such as connection to a communication computing device on the WAN 1154 or connection through the Internet. The modem 1158 which may be an internal or external and wired or wireless device is connected to the system bus 1108 through the serial port interface 1142. In the networked environment, the program modules described with respect to the computer 1102 or some thereof may be stored in the remote memory/storage device 1150. It will be well known that an illustrated network connection is exemplary and other means configuring a communication link among computers may be used.

The computer 1102 performs an operation of communicating with predetermined wireless devices or entities which are disposed and operated by the wireless communication, for example, the printer, a scanner, a desktop and/or a portable computer, a portable data assistant (PDA), a communication satellite, predetermined equipment or place associated with a wireless detectable tag, and a telephone. This at least includes wireless fidelity (Wi-Fi) and Bluetooth wireless technology. Accordingly, communication may be a predefined structure like the network in the related art or just ad hoc communication between at least two devices.

The wireless fidelity (Wi-Fi) enables connection to the Internet, and the like without a wired cable. The Wi-Fi is a wireless technology such as the device, for example, a cellular phone which enables the computer to transmit and receive data indoors or outdoors, that is, anywhere in a communication range of a base station. The Wi-Fi network uses a wireless technology called IEEE 802.11(a, b, g, and others) in order to provide safe, reliable, and high-speed wireless connection. The Wi-Fi may be used to connect the computers to each other or the Internet and the wired network (using IEEE 802.3 or Ethernet). The Wi-Fi network may operate, for example, at a data rate of 11 Mbps (802.11a) or 54 Mbps (802.11b) in unlicensed 2.4 and 5 GHz wireless bands or operate in a product including both bands (dual bands). It may be appreciated by those skilled in the art that various exemplary logical blocks, modules, processors, means, circuits, and algorithm steps described in association with the exemplary embodiments disclosed herein may be implemented by electronic hardware, various types of programs or design codes (for easy description, herein, designated as software), or a combination of all of them. In order to clearly describe the intercompatibility of the hardware and the software, various exemplary components, blocks, modules, circuits, and steps have been generally described above in association with functions thereof. Whether the functions are implemented as the hardware or software depends on design restrictions given to a specific application and an entire system. Those skilled in the art of the present disclosure may implement functions described by various methods with respect to each specific application, but it should not be interpreted that the implementation determination departs from the scope of the present disclosure.

Various exemplary embodiments presented herein may be implemented as manufactured articles using a method, a device, or a standard programming and/or engineering technique. The term manufactured article includes a computer program, a carrier, or a medium which is accessible by a predetermined computer-readable storage device. For example, a computer-readable storage medium includes a magnetic storage device (for example, a hard disk, a floppy disk, a magnetic strip, or the like), an optical disk (for example, a CD, a DVD, or the like), a smart card, and a flash memory device (for example, an EEPROM, a card, a stick, a key drive, or the like), but is not limited thereto. The term "machine-readable media" includes, but is not limited to, wireless channels and various other media that can store, retain, and/or transmit instructions and/or data.

The description of the presented exemplary embodiments is provided so that those skilled in the art of the present disclosure use or implement the present disclosure. Various modifications of the exemplary embodiments will be apparent to those skilled in the art and general principles defined herein can be applied to other exemplary embodiments without departing from the scope of the present disclosure. Therefore, the present disclosure is not limited to the exemplary embodiments presented herein, but should be interpreted within the widest range which is coherent with the principles and new features presented herein.

The invention claimed is:

1. A method for predicting an affinity between a drug and a target substance, the method performed by a computing device including at least one processor, the method comprising:
    extracting a feature value of each of the drug and the target substance by using a first neural network;
    performing a cross attention between the feature values that considers information of the target substance to align the feature value of the drug and the feature value of the target substance by using a second neural network; and
    predicting the affinity between the drug and the target substance based on a result of performing the cross attention and based on the calculated feature value of the target substance for the drug and the calculated feature value of the drug for the target substance by using a third neural network, wherein the affinity represents a binding force or force acting between the drug and the target substance;
    wherein the performing of the cross attention between the feature values by using the second neural network includes:
    generating a first key, a first query, and a first value for the drug based on the feature value of the drug, and generating a second key, a second query, and a second value for the target substance based on the feature value of the target substance;
    generating a cross attention vector based on the second query and the first key, and calculating the feature value of the target substance for the drug using the first neural network by applying the cross attention vector to the first value; and
    generating a second cross attention vector based on the first query and the second key, and calculating the feature value of the drug for the target substance using the first neural network by applying the second cross attention vector to the second value.

2. The method of claim 1, wherein the extracting of the feature value of each of the drug and the target substance by using the first neural network includes:
    extracting the feature value of the drug by using a first sub network included in the first neural network; and
    extracting the feature value of the target substance by using a second sub network included in the first neural network.

3. The method of claim 1, wherein the performing of the cross attention between the feature values by using the second neural network includes:
    calculating a feature value of the target substance for the drug by performing a cross attention which aligns the feature value of the drug and the feature value of the target substance based on a first sub network included in the second neural network; and
    calculating a feature value of the drug for the target substance by performing a cross attention which aligns the feature value of the drug and the feature value of the target substance based on a second sub network included in the second neural network.

4. The method of claim 1, wherein the generating of the cross attention vector based on the second query and the first key includes:
    generating the cross attention vector by calculating a probability value based on the second query and the first key for an entire sequence of the target substance.

5. The method of claim 4, wherein the probability value is determined based on a sparsemax function.

6. The method of claim 1, wherein the calculating of the feature value of the target substance for the drug by applying the cross attention vector to the first value includes:
    performing an element-wise operation between the cross attention vector and the first value; and
    calculating the feature value of the target substance for the drug based on a result of performing the element-wise operation.

7. The method of claim 1, wherein the generating of the second cross attention vector based on the first query and the second key includes:
    generating the second cross attention vector by calculating a probability value based on the first query and the second key for an entire sequence of the drug.

8. The method of claim 7, wherein the probability value is determined based on a sparsemax function.

9. The method of claim 1, wherein the calculating of the feature value of the drug for the target substance by applying the second cross attention vector to the second value includes:
performing an element-wise operation between the second cross attention vector and the second value; and
calculating the feature value of the drug for the target substance based on the result of performing the element-wise operation.

10. A computer program stored in a computer-readable storage medium, wherein the computer program executes following methods for predicting an affinity between a drug and a target substance when the computer program is executed by one or more processors, the method comprising:
extracting a feature value of each of the drug and the target substance by using a first neural network;
performing a cross attention between the feature values that considers information of the target substance to align the feature value of the drug and the feature value of the target substance by using a second neural network; and
predicting the affinity between the drug and the target substance based on a result of performing the cross attention and based on the calculated feature value of the target substance for the drug and the calculated feature value of the drug for the target substance by using a third neural network, wherein the affinity represents a binding force or force acting between the drug and the target substance;
wherein the performing of the cross attention between the feature values by using the second neural network includes:
generating a first key, a first query, and a first value for the drug based on the feature value of the drug, and generating a second key, a second query, and a second value for the target substance based on the feature value of the target substance;
generating a cross attention vector based on the second query and the first key, and calculating the feature value of the target substance for the drug using the first neural network by applying the cross attention vector to the first value; and
generating a second cross attention vector based on the first query and the second key, and calculating the feature value of the drug for the target substance using the first neural network by applying the second cross attention vector to the second value.

11. A computing device predicting an affinity between a drug and a target substance, comprising:
a processor including at least one core; and
a storage unit storing information related to a drug and a target substance, wherein the processor is configured to:
extract a feature value of each of the drug and the target substance by using a first neural network,
perform a cross attention between the features that considers information of the target substance to align the feature value of the drug and the feature value of the target substance by using a second neural network, and
predict the affinity between the drug and the target substance based on a result of performing the cross attention and based on the calculated feature value of the target substance for the drug and the calculated feature value of the drug for the target substance by using a third neural network, wherein the affinity represents a binding force or force acting between the drug and the target substance;
wherein the performing of the cross attention between the feature values by using the second neural network includes:
generating a first key, a first query, and a first value for the drug based on the feature value of the drug, and generating a second key, a second query, and a second value for the target substance based on the feature value of the target substance;
generating a cross attention vector based on the second query and the first key, and calculating the feature value of the target substance for the drug using the first neural network by applying the cross attention vector to the first value; and
generating a second cross attention vector based on the first query and the second key, and calculating the feature value of the drug for the target substance using the first neural network by applying the second cross attention vector to the second value.

* * * * *